United States Patent [19]
Dotolo

[11] Patent Number: 5,788,650
[45] Date of Patent: Aug. 4, 1998

[54] COLON HYDROTHERAPY APPARATUS

[75] Inventor: Raymond Dotolo, Clearwater, Fla.

[73] Assignee: Dotolo Research Corporation, Pinellas Park, Fla.

[21] Appl. No.: 910,936

[22] Filed: Aug. 8, 1997

[51] Int. Cl.$^6$ .................................................. A61B 5/00
[52] U.S. Cl. ............................................ 600/562; 604/28
[58] Field of Search .......................... 600/562; 604/27, 604/28, 29, 30, 31, 32, 33, 34, 35

[56] References Cited

U.S. PATENT DOCUMENTS

| | | | |
|---|---|---|---|
| 4,190,059 | 2/1980 | Holt | 128/227 |
| 4,626,239 | 12/1986 | Ardizzone | 604/31 |
| 4,790,811 | 12/1988 | Bloxom, Jr. | 604/27 |
| 4,874,363 | 10/1989 | Abell | 604/28 |
| 5,019,056 | 5/1991 | Lee et al. | 604/257 |
| 5,190,519 | 3/1993 | Mead et al. | 604/27 |

*Primary Examiner*—Max Hindenburg
*Assistant Examiner*—Charles Marmor, II
*Attorney, Agent, or Firm*—Donald R. Fraser

[57] ABSTRACT

A process for colonic lavage including the steps of directing pressure water of a predetermined volume and temperature through a filter for removing particulate contaminants and through a field of ultraviolet radiation and thence to irrigate a patient's colon to remove extraneous material from the colon for selective laboratory examination if required.

4 Claims, 2 Drawing Sheets

5,788,650

1

COLON HYDROTHERAPY APPARATUS

BACKGROUND OF THE INVENTION

1. Field of the Invention

The invention relates to medical apparatus used in the irrigation of a patient's colon and the withdrawal of the irrigated fluids together with any extracted solids for viewing and/or analysis and more particularly to a colonic lavage apparatus wherein the irrigated fluids are treated to remove undesired chemical substituents and to destroy bacteria and viruses to prevent the entrance thereof into the patient's colon being treated.

2. Description of the Prior Art

The prior art apparatus useful in colon hydrotherapy employs apparatus adapted to be coupled to conventional municipal water plumbing system to obtain hot and cold water under pressure. The water is then directed through suitable mixing valve means and thence through pressure regulating means. The water under the desired pressure and temperature control is directed to a speculum through a mixing manifold. The water is caused to pass through the speculum and will continuously irrigate a patient's colon extracting extraneous material deposited therein. The extracted material is caused to flow with the irrigating water back through the speculum into an evacuation line coupled with an illuminated viewing chamber in the main housing of the apparatus. The water and extracted material is then caused to exit the apparatus through a drain line having a shut-off valve. The drain line typically communicates with suitable disposal facilities such as the liner communicating with the municipal sanitary sewer, for example. The drain line may contain means for collecting a specimen of the extracted material for subsequent laboratory analysis.

A typical example of the prior art apparatus is illustrated and described in U.S. Pat. No. 4,190,059 issued to G. C. Holt on Feb. 26, 1980.

One of the objectives of apparatus of the prior art is to remove unwanted toxins and the like from the colon of a patient oftentimes for the purpose of obtaining a specimen of the extracted solid material to determine the nature of the bacteria or virus present and possibly causing discomfort and disease to the patient. It has been found that oftentimes the analyzed specimen contains bacteria and/or virus present in the transient water. Therefore, in proper analysis results, accordingly, it has been found necessary to utilize water in the apparatus which is free from bacteria and/or virus.

SUMMARY OF THE INVENTION

Accordant with the present invention, an improved apparatus has been constructed capable of economic and efficient colonic lavage and specimen extraction and collection with the use of available municipally supplied water.

It is an objective of the present invention to produce an apparatus effective for colonic lavage and specimen collection which may utilize water containing bacteria and/or viruses of the type which may be filtered and killed by filtration and/or ultraviolet radiation.

Another object of the invention is to produce an apparatus useful for colonic lavage and specimen collection which is relatively simple in construction and may be used wherever an electric power supply and a pressurized water supply are available.

The above objects as well as other objects of the invention may be typically achieved by a process for colonic lavage comprising the steps of a) directing a source of pressure water of a preselected temperature to the inlet of a pressure regulator, b) directing the water exiting the pressure regulator to the inlet of a flow regulator, c) causing the water exiting the flow regulator to pass through a filter to remove chlorine and volatile organic chemicals from the transient water, d) causing the water exiting the filter to pass through a field of ultraviolet radiation, e) directing the filtered and ultraviolet radiated water to pass into the patient's colon for lavaging same, and extracting extraneous material therein; and f) causing the water and entrained extraneous material to flow from the patient's colon to a final discharge.

BRIEF DESCRIPTION OF THE DRAWINGS

The above and other objects and advantages of the invention will become readily apparent to those skilled in the art from reading the following detailed description of the preferred embodiment of the invention when read in the light of the accompanying drawings, in which.

DETAILED DESCRIPTION OF THE PREFERRED EMBODIMENT

Figure 1:
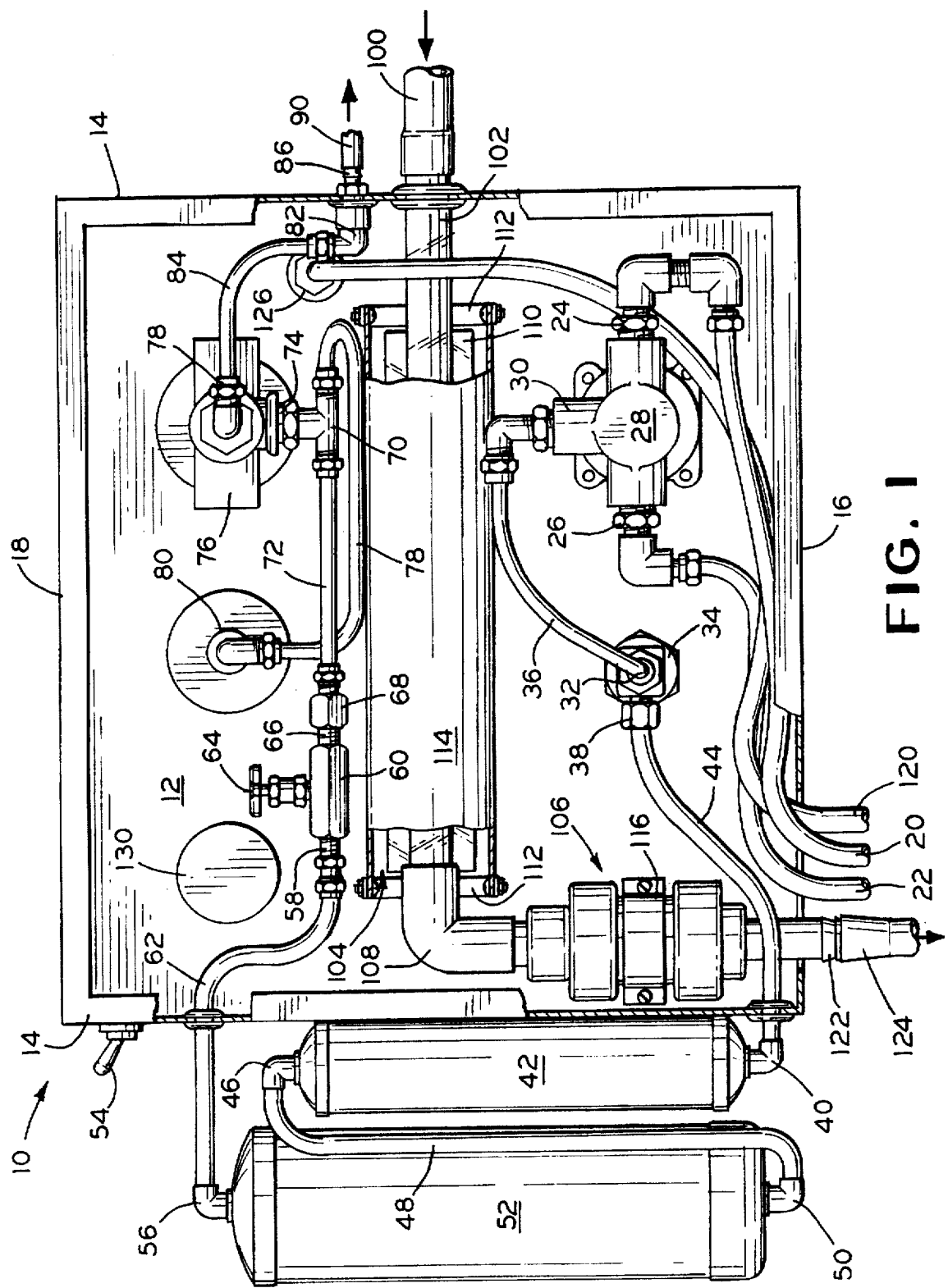
FIG. 1 is a rear elevational view of the colon hydrotherapy apparatus control panel incorporating the features of the invention.
Figure 2:
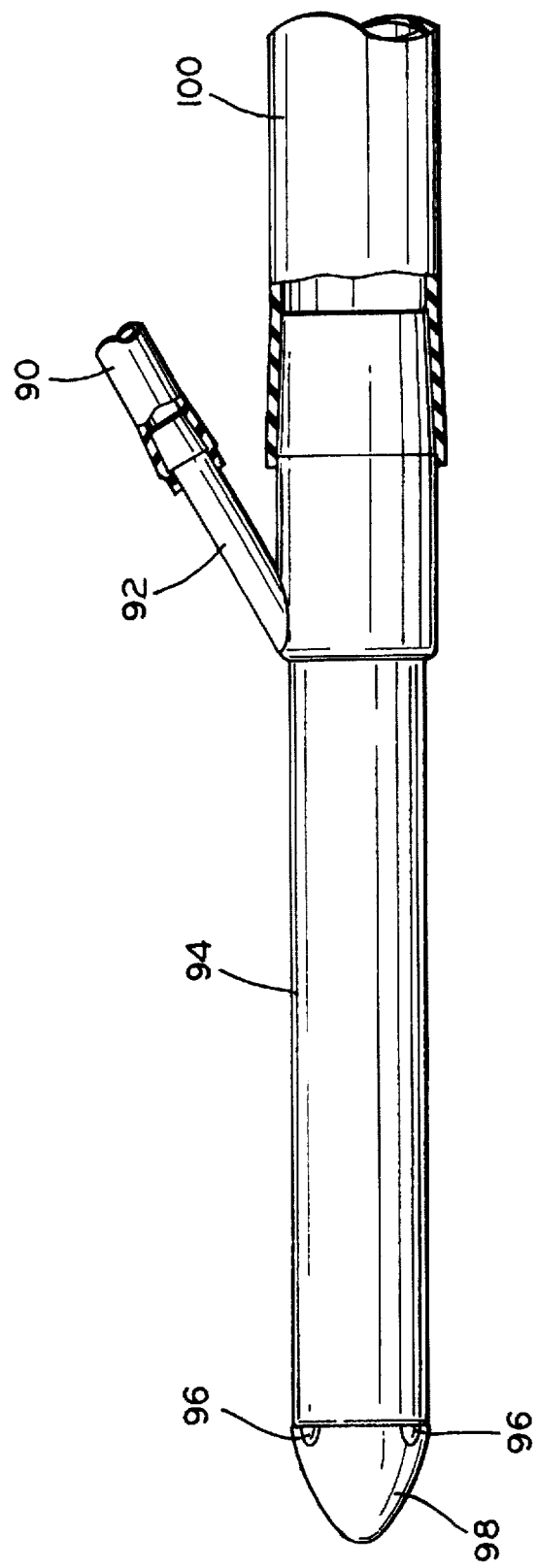
FIG. 2 is an elevational view of a speculum used in association with the apparatus illustrated in FIG. 1.

Referring to the drawings, there is illustrated a colon hydrotherapy apparatus incorporating the features of the invention. The apparatus includes a housing 10 having a front panel 12, opposing side walls 14, a bottom wall 16, and a top wall 18. The housing 10 may further include a demountable back panel, now shown.

The bottom wall 16 is provided with an opening through which a hot water conduit 20 and a cold water conduit 22 are caused to pass into the interior of the housing 10. The conduits 20, 22 are typically coupled to a hot water inlet 24 and a cold water inlet 26, respectively, of a water mixing valve 28. The mixing valve 28 is typically mounted to the front panel 12 of the housing 10. The valve 28 is controlled by a temperature adjusting handle (not shown) which is adapted to extend from the opposite side of the front panel 12. The mixing valve 28 is further provided with an outlet 30. The mixing valve 28 is designed to mix the incoming hot and cold water under pressure from the municipal water line pressure and to exit the valve through the outlet 30 at a desired temperature.

The water emerging from the outlet 30 of the mixing valve 28 is directed to the inlet 32 of a conventional water pressure control valve 34 through a conduit 36. The valve 34 is typically mounted on the front panel 12 in a usual manner and is provided with pressure regulating knob (not shown) which is adapted to extend outwardly of the opposite surface of the front panel 12. The control valve 34 is further provided with an outlet 38.

The outlet 38 of the control valve 34 is coupled to the inlet 40 of a filter housing 42 through a conduit 44. The filter housing 42 is disposed adjacent the outer surface of one of the end walls 14 and is secured to the housing 10 by means of suitable brackets (not shown). The filter housing 42 may be provided with removable end caps enabling access to the interior thereof for the insertion or removal of an activated carbon filter cartridge, for example. Activated carbon filters are useful in the reduction of the chlorine content in the transient water. Also, activated carbon will aid in the reduction of organic materials (both synthetic organic chemicals including pesticides and herbicides, and volatile organic compounds).

The filter housing 42 is further provided with an outlet 46 which is coupled to the inlet 50 of a ultraviolet chamber 52 through a conduit 48. The chamber 52 is provided with a source of ultraviolet radiation disposed within the chamber 52 and coupled to a source of electrical power (not shown) through suitable electrical conductors (not shown) and a switch 54. The chamber 52 has an outlet 56 which is coupled to the inlet 58 of a pressure limiting valve 60 through a conduit 62.

The pressure limiting valve 60 is a conventional type adapted to adjustably restrict the flow rate of water passing therethrough. The adjustment of flow rate is typically accomplished by a handle 64.

The water pressure control valve 34 and the water pressure limiting valve 60 cooperate to form a water pressure regulating valve means which functions to limit the maximum pressure of the water and to provide pressure adjustment below the maximum preset pressure limit. Typically, the pressure limiting valve 60 is preset to assure that the water exiting the outlet 66 thereof will not exceed a pressure of approximately 5 psi. The pressure control valve 34 is employed to allow the water pressure to vary in the range of from 0-5 psi.

The pressure and temperature regulated water emerging from the outlet 66 is adapted to pass through a check valve 68 and thence to a tee 70, through a conduit 72, one outlet branch of which is threadably connected to an inlet 74 of a temperature gauge 76. The temperature gauge 76 is typically mounted on the front panel 12 and is adapted to protrude from the front or opposite surface of panel 12 for convenient viewing of an associated dial face (not shown). The water mixing valve 28 and the temperature gauge 76 cooperate to provide means for precision temperature control of the water.

The other outlet branch of the tee 70 is connected to a pressure gauge 80 through a conduit 78. As with the temperature gauge 76, the pressure gauge 80 is mounted to the front panel 12 with the dial face thereof protruding through an aperture in the panel 12 enabling the viewing thereof from the front of the apparatus. The pressure gauge 80, the pressure control valve 34, and the pressure limiting valve 60 cooperate to provide the apparatus of the invention with precision control of the pressure of the water within the system.

The water, regulated as to pressure and temperature, is adapted to exit an outlet 78 of the temperature gauge 76 and is directed to an outlet fitting 82 through a conduit 84. The outlet fitting 82 is mounted to extend through a side wall 14 and the housing 10 and is provided with a hose barb or bayonet type coupling element 86 for receiving one end of a water supply conduit 90.

The water supply conduit 90 extends from the housing 10 and has its other end connected to the inlet of an inlet pipe 92 which in turn communicates with a mixing chamber within a speculum 94. The speculum 94 may have an annular array of outlets 96 formed in a water soluble insert 98 fitting in the end of the speculum 94 remote from the inlet pipe 92. The insert 98 is gently tapered. The speculum 94 is adapted for insertion into the anal canal of a patient. Thus, the water entering the inlet 92 will pass through the speculum 94 into the colon of a patient where it will act to loosen material which has become lodged therein by an irrigation process. When the colon becomes full of water, a reverse flow will commence so that the water and the extracted material will flow back through the speculum 94, through a conduit 100 secured to the outlet end of the speculum 94 opposite the insert 98. The water and extracted material is then caused to flow through the conduit 100, the other end of which is connected to an inlet end of an optically transparent sight tube 102 which extends through the side wall 14 of the housing 10. The sight tube 102 passes through an illuminated viewing chamber 104 disposed within the housing 10 and has its outlet end coupled to the inlet end of a drain shutoff valve 106 through an elbow 108.

The illuminated viewing chamber 104 includes a transparent sheet material 110 adapted to span an opening formed in the front panel 12. A pair of spaced apart U-shaped brackets 112 are mounted on the interior surface of the front panel 12 adjacent respective ends of the opening in the front panel 12. An elongate translucent panel 114, which is arcuate in cross-section, is held in position by having its opposite ends attached to the brackets 112. A fluorescent light (not shown) is mounted in an usual manner immediately adjacent to and behind the translucent sheet 114. The light is coupled to a source of electrical energy through suitable electric wiring (not shown) including the electrical on/off switch 54.

The illuminated viewing chamber 104 having the sight tube 102 passing through the space between the transparent sheet 110 and the arcuate translucent panel 114 is provided so that the extracted material may be visually inspected by the operator during colonic irrigation oftentimes referred to as colonic hydrotherapy.

The drain shutoff valve 106 is mounted to the front panel 12 by suitable bracket 116 and is a conventional type device typically provided with a handle operable from the front of the front panel 12. The handle (not shown) may be manually movable between open and closed position. The outlet end of the drain valve 106 is provided with a barbed or threaded nipple 122 upon which one end of a drain conduit 124 is coupled.

As illustrated in FIG. 1, there is shown the rear view of an oxygen pressure regulator and shut-off valve assembly 126 suitably mounted on the front panel 12. The assembly 126 includes a viewing scale and manually operated valve (not shown) mounted on the exposed front surface of the panel 12. The oxygen valve 126 includes a shut-off knob located at the upper end and a pressure regulating knob mounted at the lower end. Oxygen under pressure from a remote source is supplied through a conduit 120 to an inlet of the valve 126. The outlet of the valve 126 is coupled to the speculum 94 through a connection with the outlet 82 or alternatively may be connected to the speculum 94 through a separate conduit connected to the inlet pipe 90.

The apparatus may be further provided with a timing device 130 which is adapted to be mounted on the front panel 12. The timing device 130 may be used to time the duration of the colonic lavage administered to a patient. It will be understood that the timer 130 is a desirable accessory, but does not enter directly into the function of the apparatus described above.

It will be understood that in the preferred embodiment of the invention the filter cartridge utilized in the filter 42 is typically comprised of activated carbon which has a number of uses. Activated carbon is typically useful for taste and odor control for potable water, chlorine reduction, organic reduction, and reduction of hazardous organic chemicals. These features are sometimes combined in a single application, but they have distinctly different objectives. The fact that they are different is something that which must be kept in mind. While some activated carbons are excellent for one application, they may not be suited for another.

Although there are different uses for activated carbon, the actual absorption mechanism is the same. There are common media materials and media types, such as powdered, granular, and block carbon. However, it will be understood that the activated carbon is effective in adsorbing organic molecules such as herbicides, pesticides, and industrial solvents. The activated carbon is literally riddled with a network of tiny tunnels (pores) that are produced during the activation process and provide a very large surface area to attract the containments.

Further, the micro-organisms exposed to the ultraviolet radiation within the chamber 52 are destroyed because the ultraviolet radiation scrambles the DNA structure prohibiting reproduction thereof. The time interval the transient water is exposed and the intensity of the radiation are factors in bacterial reduction. Typically, the proper exposure should be greater than 16,000 microwatt-seconds/centimeters squared for successful water treatment.

In accordance with the provisions of the patent statutes, the present invention has been described in what is considered to represent its preferred embodiment. However, it should be understood that the invention can be practiced otherwise than as specifically illustrated and described without departing from its spirit or scope.

What is claimed is:

1. A process for colonic lavage wherein water under pressure is directed through a speculum into a patient's colon comprising the steps of:
   a) directing a source of pressure water of a preselected flow rate and temperature to the inlet of a filter;
   b) causing the water to pass through the filter to the outlet thereof to remove particulate contaminants from the transient water;
   c) directing the filtered water exiting the outlet of the filter through a field of ultraviolet radiation;
   d) directing the filtered and ultraviolet irradiated water to pass into a patient's colon for lavaging same and extracting extraneous material therefrom; and
   e) causing the water and entrained extraneous material to flow from the patient's colon to a viewing and discharge station.

2. A process as defined in claim 1 wherein step e) includes the additional step of removing a sample of the extraneous material for laboratory examination.

3. A process for colonic lavage wherein water under pressure is directed through a speculum into a patient's colon comprising the steps of:
   a) directing a source of pressure water of a preselected temperature to the inlet of a pressure regulator;
   b) directing the water exiting the pressure regulator to the inlet of a flow regulator;
   c) causing the water exiting the flow regulator to pass through a filter to remove particulate contaminants from the transient water;
   d) causing the water exiting the filter to pass through a field of ultraviolet radiation;
   e) directing the filtered and ultraviolet radiated water to pass into the patient's colon for lavaging same, and entraining extraneous material therein; and
   f) causing the water and entrained extraneous material to flow from the patient's colon to a final discharge.

4. A process for colonic lavage as defined in claim 3 wherein the particulate contaminants removed in step c) include chlorine and volatile organic chemicals.

* * * * *